United States Patent [19]

Ishii et al.

[11] 3,972,920

[45] Aug. 3, 1976

[54] PROCESS FOR PRODUCING UNSATURATED ALDEHYDES, UNSATURATED FATTY ACIDS OR CONJUGATED DIENES

[75] Inventors: Hiromichi Ishii; Hideo Matsuzawa; Masao Kobayashi, all of Ohtake; Kantaro Yamada, Yokohama, all of Japan

[73] Assignee: Mitsubishi Rayon Co., Ltd., Tokyo, Japan

[22] Filed: May 29, 1974

[21] Appl. No.: 474,218

[30] Foreign Application Priority Data

June 11, 1973 Japan.................................. 48-65563
Aug. 28, 1973 Japan.................................. 48-96345
Dec. 18, 1973 Japan................................. 48-142118
Dec. 26, 1973 Japan................................. 48-144000

[52] U.S. Cl................................ 260/531 R; 252/469; 252/470; 260/533 N; 260/603 HF; 260/604 R; 260/680 E
[51] Int. Cl.².................... C07C 51/24; C07C 51/32
[58] Field of Search........ 260/533 N, 604 R, 680 E, 260/531 R, 603 HF

[56] References Cited

UNITED STATES PATENTS

| | | | |
|---|---|---|---|
| 3,470,239 | 9/1969 | Russell........................... | 260/604 R |
| 3,642,930 | 2/1972 | Grasselli et al................. | 260/533 N |
| 3,825,502 | 7/1974 | Takenaka et al............... | 260/604 R |
| 3,892,794 | 7/1975 | Grasselli et al............. | 260/533 N X |

FOREIGN PATENTS OR APPLICATIONS

| | | | |
|---|---|---|---|
| 2,000,425 | 6/1970 | Germany........................ | 260/533 N |

*Primary Examiner*—Richard L. Raymond
*Attorney, Agent, or Firm*—Oblon, Fisher, Spivak, McClelland & Maier

[57] ABSTRACT

Methacrolein is produced by catalytically oxidizing t-butyl alcohol with oxygen by using a catalyst system of MoSbBiFeNi-alkali. Propylene or isobutylene can also be catalytically oxidized with the same catalyst system to produce acrolein or methacrolein. Methacrolein and 1,3-butadiene can simultaneously be produced by catalytically oxidizing a mixture of isobutylene and n-butene with the same catalyst.

8 Claims, No Drawings

PROCESS FOR PRODUCING UNSATURATED ALDEHYDES, UNSATURATED FATTY ACIDS OR CONJUGATED DIENES

This invention relates to a process for producing unsaturated aldehydes, unsaturated fatty acids or conjugated dienes by catalytic oxidation of t-butyl alcohol, or unsaturated hydrocarbons with carbon atoms of 3 to 4.

There have heretofore been known various processes for catalytic oxidation of propylene or isobutylene to obtain corresponding unsaturated aldehydes. Japanese Pat. No. 32049/72 discloses a catalyst comprising molybdenum, antimony, bismuth, iron, nickel and oxygen and a catalyst wherein tin is further added to said catalyst. When propylene is oxidized catalytically by the use of productivity catalyst, the total selectivity of acrolein and acrylic acid reaches as much as 90 to 91 % where the conversion of propylene is 95 %, but the amount of the by-products is comparatively large, namely, the total selectivity of carbon mono-oxide and carbon dioxide is as much as 6 to 8%. On the other hand, when isobutylene is oxidized by using this catalyst, carbon monooxide and carbon dioxide are by-produced in so increased amounts that selectivity of methacrolein is lowered. From an industrial standpoint, favorable results such as improvement producitivity and removal of reaction heat are brought about by suppressing formation of by-produced gases as far as possible. A process for producing methacrolein by gas phase oxidation of t-butyl alcohol is disclosed by Japanese Pat. Laying-open No. 32814/73. The catalyst used in this process contains thallium, but yield of methacrolein in a catalyst system not containing thallium is about 40 %.

The present inventors have made studies over catalysts not containing thallium and at last found a novel catalyst effective for catalytic oxidation of both isobutylene and t-butyl alcohol.

An object of the present invention is to provide a novel catalyst for producing methacrolein in high yield from isobutylene or t-butyl alcohol.

The other object of the present invention is to provide a novel catalyst for producing methacrolein and 1,3-butadiene in high yield by simultaneously oxidizing isobutylene and n-butene.

According to the present invention, there is provided a process for oxidizing isobutylene, isobutylene and n-butene, or t-butyl alcohol catalytically in gas phase by using a catalyst having the general formula:

$$Mo_a Sb_b Bi_c Fe_d Ni_e Sn_f X_g Y_h O_i$$

wherein X is at least one alkali metal selected from potassium, rubidium and cesium, Y is at least one metal selected from palladium, cobalt, uranium, germanium, tungsten, and titanium, a to h show atomic ratios within the range that when $a=12$, $b=0.2$ to 20, $c=0.2$ to 12, $d=0.2$ to 12, $e=0.2$ to 12, $f=0$ to 20, $g=0.01$ to 4, $h=0$ to 6 and $i$ is a value determined according to the state of oxidation.

Acrolein can also be produced by using the catalyst as represented by the above general formula.

The catalyst of the present invention can be prepared by a known method. As the source for molybdenum in preparation of the catalyst, an oxide or a compound convertible on heating into and oxide is desirable. As such a compound, there is ammonium molybdate. As the sources for antimony and tin, oxides, hydrate oxides, chlorides thereof are preferred. As the sources for bismuth, iron, nickel and alkali metal, oxides or compounds convertible on heating into oxides, such as nitrates, carbonates or hydroxides, are preferred. In preparation of the catalyst, carriers may be used. As the carriers, silica, alumina or silicon carbide may be used. The atomic ratios of each component in the catalyst can be varied within the range as mentioned above. The particularly preferable range is that when $a$ is 12, $b=0.5$ to 20, $c=0.5$ to 6, $d=0.5$ to 6, $e=0.5$ to 6 and $g=0.01$ to 2. When tin is added to the catalyst, the strength of the catalyst is increased and the catalyst life is made longer. The amount of tin added is, in terms of the atomic ratio, $f=0.5$ to 12 when $a$ is 12.

By addition of palladium, cobalt, uranium, germanium, tungsten or titanium to the catalyst, the reaction temperature can be lowered and yield of methacrolein is improved. As the sources for these metals, oxides or compounds convertible on heating to oxides are used. The amount of these metals added is preferably, in terms of the atomic ratio, $h=0.01$ to 3 when $a$ is 12.

In carrying out the reaction of the present invention, starting materials such as isobutylene, a mixture of isobutylene and n-butene or t-butyl alcohol are preferably diluted with inert gases. As inert gases, nitrogen, steam or carbon dioxide may be used. In particular, steam influences favorably the improvement in yield. As the oxygen source to be used for oxidation, air or air enriched in oxygen is used. The concentration of propylene, isobutylene or t-butyl alcohol can be varied within the range of 1 to 20 vol.%. The concentration of oxygen may also be varied within the range of 1 to 20 vol. %.

The reaction pressure is from normal pressure to several atm. The reaction temperature is from 200° to 450°C, particularly preferably from 250° to 400°C. The contact time is preferably from 0.5 to 10 seconds. The reaction may be carried out either in a fixed bed or a fluidized bed.

The present invention is illustrated in further detail by referring to the following Examples, wherein "parts" signifies "parts by weight", and yield is calculated by the following equation:

Yield =  × 100 where the numerator is "Title product (methacrolein, methacrylic acid or 1,3-butadiene:moles" and the denominator is "Starting material charged (moles)"

EXAMPLE 1

In 200 parts of water are suspended 27.6 parts of fine powders of antimony pentoxide and a solution of 42.5 parts of ammonium molybdate dissolved in 200 parts of water is added thereto. Then, a solution of 1.0 part of potassium nitrate dissolved in 10 parts of water, a solution of 48.5 parts of bismuth nitrate dissolved in 50 parts of 10 % nitric acid and a solution of 16.4 parts of ferric nitrate and 5.9 parts of nickel nitrate dissolved in 100 parts of water are added in this order to the mixture. Finally, 45 parts of silica are added as carrier in the form of silica sol. The slurry obtained is evaporated to dryness, dried at 120°C and thereafter pelletted, followed by calcination at 500°C for 6 hours. The catalyst is packed in a reaction tube, heated to 305°C in an air bath, and a mixed feed gas containing 6 % propylene, 12 % oxygen, 47 % nitrogen and 35 % steam (all in mole %) is passed therethrough at a contact time of 3.6 seconds. The gas formed is analyzed by gas chromatography to obtain the result that the total yield of acrolein and acrylic acid is 89.7 %.

EXAMPLE 2

By the use of the catalyst of Example 1, a mixed feed gas containing 5 % t-butyl alcohol, 12 % oxygen, 48 % nitrogen and 35 % steam (all in mole %) is introduced into the catalyst layer maintained at 385°C and passed therethrough at a contact time of 3.6 seconds. As the result of analysis of the formed gas by gas chromatography, the total yield of methacrolein and methacrylic acid is 78.0 %.

EXAMPLE 3

By the use of the catalyst of Example 1, a mixed gas containing 5.4 % mixed butenes (having the composition of 39 % 1-butene, 10 % cis-2-butene, 10 % trans-2-butene and 41 % isobutylene), 12.6 % oxygen, 35 % steam and 47 % nitrogen (all in mole %) is introduced into the catalyst layer maintained at 360°C and reacted at a contact time of 3.6 seconds. As the result of analysis of the gas formed by gas chromatography, per-pass yield of butadiene from n-butenes is 76.0 % and the total yield of methacrolein and methacrylic acid from isobutylene is 77.7 %.

EXAMPLE 4

By using a catalyst having the same composition as in the catalyst of Example 1 except that 1.5 parts of rubidium nitrate are further added, the reaction is carried out under the same conditions as in Example 1 except that the bath temperature is maintained at 310°C to obtain the result that the total yield of acrolein and acrylic acid is 92.0 %.

EXAMPLE 5

By using the same catalyst as used in Example 4, the reaction is carried out under the same conditions as in Example 3 to obtain the result that the per-pass yield of butadiene from n-butenes is 76.6 % and the total yield of methacrolein and methacrylic acid from isobutylene is 79.6 %.

EXAMPLE 6

By using a catalyst having the same composition as used in Example 1 except that 0.78 parts of cecium nitrate are further added, the reaction is carried out under the same conditions except that the bath temperature is maintained at 310°C to obtain the result that the total yield of acrolein and acrylic acid is 91.7 %.

EXAMPLE 7

By using the catalyst of Example 6, a mixed feed gas containing 6 % isobutylene, 12 % oxygen, 47 % nitrogen and 35 % steam (all in mole %) is passed at a contact time of 3.6 seconds. The total yield of methacrolein and methacrylic acid is found to be 75.8 %.

EXAMPLE 8

When the reaction is conducted by using the catalyst of Example 6 and maintaining the bath temperature at 365°C, otherwise being under the same conditions as in Example 3, the per-pass yield of butadiene from n-butenes and the total yield of methacrolein and methacrylic acid from isobutylene are found to be 79.2 % and 77.9 %, respectively.

EXAMPLE 9

When the reaction is conducted by using the same catalyst as used in Example 6 and maintaining the bath temperature at 380°C, otherwise being under the same conditions as in Example 2, the total yield of methacrolein and methacrylic acid is found to be 81.5 %.

EXAMPLE 10

In 200 parts of water are suspended 27.6 parts of finely powdered antimony pentoxide and a solution of 42.5 parts of ammonium molybdate dissolved in 200 parts of water is added to this suspension. Then, a solution of 2.0 parts of potassium nitrate dissolved in 10 parts of water, a solution of 29.1 parts of bismuth nitrate dissolved in 50 parts of 10 % nitric acid and a solution of 8.2 parts of ferric nitrate and 11.8 parts of nickel nitrate dissolved in 100 parts of water are added in this order to the mixture. Furthermore, a solution of 14.4 parts of stannous chloride dissolved in 50 parts of 10 % nitric acid is added to the mixture and finally 45 parts of silica sol are added thereto. The slurry obtained is evaporated to dryness, dried at 120°C and thereafter pelleted, followed by calcination at 500°C for 6 hours. By using this catalyst, and maintaining the bath temperature at 300°C, the reaction is performed under otherwise the same conditions as in Example 1. As the result, total yield of acrolein and acrylic acid is found to be 91.0 %.

EXAMPLE 11

The reaction is performed by using the same catalyst as used in Example 10 and maintaining the bath temperature at 375°C under otherwise the same conditions as in Example 7. As the result, the total yield of methacrolein and methacrylic acid is found to be 77.0 %.

EXAMPLE 12

The reaction is performed by using the same catalyst as used in Example 10 and maintaining the bath temperature at 350°C under otherwise the same conditions as in Example 3. The result is that per-pass yield of butadiene from n-butenes is 76.0 % and the total yield of methacrolein and methacrylic acid is 78.8 %.

EXAMPLE 13

When the reaction is performed by using the same catalyst as used in Example 10 and maintaining the bath temperature at 375°C, otherwise being under the same conditions as in Example 2, the total yield of methacrolein and methacrylic acid is found to be 79.0 %.

EXAMPLE 14

In 200 parts of water are suspended 27.6 parts of finely powdered antimony pentoxide and a solution of 42.5 parts of ammonium molybdate dissolved in 200 parts of water is added to this suspension. Then, a solution of 1.0 part of potassium nitrate and 0.78 parts of cesium nitrate dissolved in 20 parts of water, a solution of 48.5 parts of bismuth nitrate dissolved in 50 parts of 10 % nitric acid, a solution of 16.4 parts of ferric nitrate, 5.9 parts of nickel nitrate and 11.6 parts of cobalt nitrate dissolved in 100 parts of water and a solution of 0.92 parts of palladium nitrate dissolved in 20 parts of water are added in this order to the mixture, followed finally by addition of 45 parts of silica as carrier in the form of silica sol. The slurry obtained is evaporated to dryness and dried at 120°C, then pelleted and calcined at 500°C under air stream for 6 hours to provide a catalyst.

EXAMPLE 15

A catalyst is prepared in the same manner as in Example 14 except that no cobalt nitrate is added and 1.5 parts of rubidium nitrate are used in place of cesium nitrate.

EXAMPLE 16

A catalyst is prepared in the same manner as in Example 14 except that none of cesium nitrate, cobalt nitrate and palladium nitrate are added but 1.05 parts of germanium oxide are added.

EXAMPLE 17

A catalyst is prepared in the same manner as in Example 14 except that none of cesium nitrate, palladium nitrate and cobalt nitrate are added but 2.7 parts of ammonium tungstate are added.

EXAMPLE 18

A catalyst is prepared in the same manner as in Example 14 except that none of cesium nitrate, palladium nitrate and cobalt nitrate are added but 3.2 parts of titanium oxide are added.

EXAMPLE 19

A catalyst is prepared in the same manner as in Example 14 except that none of cesium nitrate, palladium nitrate and cobalt nitrate are added but 10.0 parts of uranyl nitrate are added.

EXAMPLE 20

In 200 parts of water are suspended 27.6 parts of finely powdered antimony pentoxide and a solution of 42.5 parts of ammonium molybdate dissolved in 200 parts of water is added to this suspension. Then, a solution of 2.0 parts of potassium nitrate dissolved in 10 parts of water, a solution of 29.1 parts of bismuth nitrate dissolved in 50 parts of 10 % nitric acid, a solution of 8.2 parts of ferric nitrate and 11.8 parts of nickel nitrate dissolved in 100 parts of water and a solution of 5.0 parts of uranyl nitrate dissolved in 20 parts of water are added in this order to the mixture, followed further by addition of a solution of 14.4 parts of stannous chloride dissolved in 50 parts of 10 % nitric acid and finally by addition of 45 parts of silica sol. The slurry obtained is evaporated to dryness, dried at 120°C, then pelleted and calcined at 500°C for 6 hours. The product is used as a catalyst.

EXAMPLE 21

A catalyst is prepared in the same manner as in Example 20 except that no uranyl nitrate is added but 5.8 parts of cobalt nitrate are added.

EXAMPLE 22

A catalyst is prepared in the same manner as in Example 20 except that 0.46 parts of palladium nitrate and 1.6 parts of titanium oxide are further added.

Each catalyst prepared in Examples 14 to 22 is used in respective reaction wherein a mixed feed gas containing 5 % t-butyl alcohol, 12 % oxygen, 48 % nitrogen and 35 % steam (all in mole %) is introduced into the catalyst layer maintained at respective temperature and passed therethrough at a contact time of 3.6 seconds. The gases formed are analyzed to obtain the result as shown in Table 1.

Table 1

| Example No. | Catalyst elements | Reaction temperature (°C) | Yield of methacrolein and methacrylic acid (%) |
|---|---|---|---|
| 14 | Mo—Sb—Bi—Fe—Ni—K—Cs—Pd—Co | 330 | 84.0 |
| 15 | Mo—Sb—Bi—Fe—Ni—K—Rb—Pd | 350 | 83.7 |
| 16 | Mo—Sb—Bi—Fe—Ni—K—Ge | 345 | 82.5 |
| 17 | Mo—Sb—Bi—Fe—Ni—K—W | 360 | 81.0 |
| 18 | Mo—Sb—Bi—Fe—Ni—K—Ti | 355 | 82.2 |
| 19 | Mo—Sb—Bi—Fe—Ni—K—U | 365 | 81.5 |
| 20 | Mo—Sb—Bi—Fe—Ni—Sn—K—U | 350 | 82.3 |
| 21 | Mo—Sb—Bi—Fe—Ni—Sn—K—Co | 355 | 83.5 |
| 22 | Mo—Sb—Bi—Fe—Ni—Sn—K—U—Pd—Ti | 340 | 83.1 |

What is claimed is:
1. In a process for producing corresponding aldehydes, acids or conjugated dienes by gas phase catalytic oxidation of at least one compound selected from the group consisting of unsaturated hydrocarbons with 3 to 4 carbon atoms and t-butyl alcohol by using molecular oxygen at 200°–450°C, the improvement comprising: oxidizing said compound over a calcined catalyst consisting essentially of

$$Mo_aSb_bBi_cFe_dNi_eSn_fX_gY_hO_i$$

wherein X is at least one alkali metal selected from the group consisting of potassium, rubidium and cesium, Y is palladium, suffixes $a$ to $h$ are atomic ratios, wherein $a=12$, $b=0.5$ to 20, $c=0.5$ to 6, $d=0.5$ to 6, $e=0.5$ to 6, $f=0$ to 20, $g=0.01$ to 2 and $h=0.01$ to 3, and i is determined according to the state of oxidation of said catalyst.

2. A process according to claim 1 wherein t-butyl alcohol is catalytically oxidized in gas phase to produce superior amount of methacrolein and inferior amount of methacrylic acid.

3. A process according to claim 1 wherein a mixture of isobutylene and n-butene is catalytically oxidized in gas phase to produce methacrolein, a small amount of methacrylic acid and 1,3-butadiene.

4. A process according to claim 1 wherein isobutylene is catalytically oxidized in gas phase to produce superior amount of methacrolein and inferior amount of methacrylic acid.

5. A process according to claim 1 wherein propylene is catalytically oxidized in gas phase to produce superior amount of acrolein and inferior amount of acrylic acid.

6. A process according to claim 1 wherein the component X is potassium.

7. A process according to claim 1 wherein the component X is cesium.

8. A process according to claim 1 wherein the component X is potassium and cesium.

* * * * *